(12) United States Patent
Fan

(10) Patent No.: US 7,874,728 B2
(45) Date of Patent: Jan. 25, 2011

(54) X-RAY IMAGING APPARATUS AND PORTABLE DETECTOR PANEL

(75) Inventor: Yi Fan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/358,856

(22) Filed: Jan. 23, 2009

(65) Prior Publication Data

US 2009/0190718 A1 Jul. 30, 2009

(30) Foreign Application Priority Data

Jan. 25, 2008 (CN) .................... 2008 1 0085629

(51) Int. Cl.
*H05G 1/02* (2006.01)
(52) U.S. Cl. .................... 378/198; 378/102; 378/98.8
(58) Field of Classification Search ................ 378/98.8, 378/198, 101–103
See application file for complete search history.

(56) References Cited

U.S. PATENT DOCUMENTS

| | | | |
|---|---|---|---|
| 4,681,227 A | 7/1987 | Tamura et al. | |
| 4,922,105 A | 5/1990 | Hosoi | |
| 5,081,543 A | 1/1992 | Romandi | |
| 5,514,873 A | 5/1996 | Schulze-Ganzlin et al. | |
| 5,804,832 A | 9/1998 | Crowell et al. | |
| 5,877,501 A | 3/1999 | Ivan et al. | |
| 5,912,941 A | 6/1999 | Schmitt | |
| 6,091,982 A | 7/2000 | Reinke et al. | |
| 6,205,119 B1 | 3/2001 | Kaczynski | |
| 6,575,624 B2 | 6/2003 | Noegel et al. | |
| 6,700,126 B2 | 3/2004 | Watanabe | |
| 6,825,472 B2 | 11/2004 | Endo | |
| 7,016,467 B2 | 3/2006 | Brooks | |
| 7,057,181 B2 | 6/2006 | Yagi | |
| 7,078,703 B2 | 7/2006 | Watanabe | |
| 7,164,137 B2 | 1/2007 | Hayashida | |
| 7,189,972 B2 | 3/2007 | Ertel et al. | |
| 7,202,481 B2 | 4/2007 | Spahn et al. | |
| 7,317,190 B2 | 1/2008 | Ertel et al. | |
| 7,342,998 B2 | 3/2008 | Kump et al. | |
| 7,396,159 B2 | 7/2008 | Utschig et al. | |
| 7,429,737 B2 | 9/2008 | Wojcik et al. | |
| 7,435,967 B2 | 10/2008 | Ertel et al. | |
| 7,488,946 B2 | 2/2009 | Hennessy et al. | |
| 7,495,226 B2 | 2/2009 | Jadrich et al. | |
| 7,581,883 B2 | 9/2009 | Kato | |
| 2002/0150214 A1 | 10/2002 | Spahn | |
| 2006/0034427 A1 * | 2/2006 | Brooks | 378/198 |

FOREIGN PATENT DOCUMENTS

JP 2002-336227 11/2002

* cited by examiner

*Primary Examiner*—Courtney Thomas
(74) *Attorney, Agent, or Firm*—Armstrong Teasdale LLP

(57) ABSTRACT

An X-ray imaging apparatus includes: a mobile system console with an X-ray irradiator and a control circuit; and a portable detector panel with an X-ray detector, an interface electronic circuit, and a power supply battery. The system console includes an accommodating section for accommodating the detector panel at the time of nonuse, and the detector panel includes feeding control device for unexecuting and executing feeding to the electronic circuit from the battery according to the accommodation and non-accommodation in the accommodating section, respectively.

20 Claims, 7 Drawing Sheets

X-RAY IMAGING APPARATUS AND PORTABLE DETECTOR PANEL

CROSS REFERENCE TO RELATED APPLICATIONS

This application claims the benefit of Chinese Patent Application No. 200810085629.5 filed Jan. 25, 2008, which is hereby incorporated by reference in its entirety.

BACKGROUND OF THE INVENTION

The embodiments described herein relate to an X-ray imaging apparatus and a portable detector panel, and more particularly to an X-ray imaging apparatus that detects, through an X-ray detector, X-rays that are irradiated from an X-ray irradiator and penetrate an object to be detected, and photographs a fluoroscopic image, and a portable detector panel that is used in the X-ray imaging apparatus.

One type of the X-ray imaging apparatuses is a mobile type. The X-ray imaging apparatus of this type is made up of a mobile system console and a portable detector panel. The system console includes an X-ray irradiator and a control circuit, and the detector panel includes an X-ray detector, an interface electronic circuit, and a power supply battery therein.

The X-ray photography is conducted after the X-ray imaging apparatus moves to a patient's room. The photography in the patient's room is conducted by applying the detector panel on a patient's portion to be photographed and irradiating an opposite side of the portion with X-rays. The X-ray signal which has been detected by the detector panel is transmitted to the system console in a wired or wireless manner (for example, refer to Japanese Unexamined Patent Publication No. 2002-336227 (paragraphs 0017 to 0020, FIG. 1)).

BRIEF DESCRIPTION OF THE INVENTION

In order to effectively use the electric power of a battery, it is desirable that the feeding to a load is conducted only when the detector panel is used, but not conducted when the detector panel is not used. Also, it is desirable that the changeover between the feeding and non-feeding is automatically conducted not depending on the switch operation.

Under the above circumstances, an X-ray imaging apparatus of the mobile type is provided which conducts the feeding and non-feeding to the load from a built-in battery in association with the use or nonuse of the detector panel, and a portable detector panel for the X-ray imaging apparatus.

In order to solve the above problem, according to a first aspect of the present invention, there is provided an X-ray imaging apparatus having: a mobile system console with an X-ray irradiator and a control circuit; and a portable detector panel with an X-ray detector, an interface electronic circuit, and a power supply battery, wherein the system console includes an accommodating section for accommodating the detector panel at the time of nonuse, and wherein the detector panel includes feeding control device for unexecuting and executing feeding to the electronic circuit from the battery according to the accommodation and non-accommodation in the accommodating section, respectively.

In order to solve the above problem, according to a second aspect of the present invention, there is provided the X-ray imaging apparatus according to the first aspect, wherein the accommodating section and the detector panel respectively includes connection sections that are electrically connected to each other at the time of accommodating the detector panel.

In order to solve the above problem, according to a third aspect of the present invention, there is provided the X-ray imaging apparatus according to the second aspect, wherein the accommodating section includes a plug or an outlet, and wherein the detector panel includes an outlet or a plug corresponding to the plug or the outlet of the accommodating section.

In order to solve the above problem, according to a fourth aspect of the present invention, there is provided the X-ray imaging apparatus according to the second or third aspect, wherein the connection section of the accommodating section is disposed on a bottom of the accommodating section, and wherein the connection section of the detector panel is disposed on an end surface of the detector panel which is abutted against the bottom of the accommodating section.

In order to solve the above problem, according to a fifth aspect of the present invention, there is provided the X-ray imaging apparatus according to the third aspect, wherein the plug has three parallel conductors, a center conductor is connected to the ground, and both-side conductors are commonly connected to each other, and wherein the outlet has three receivers corresponding to the conductors, a center receiver functions as a common receiver, one of the remaining two receivers is connected with a pull-down resistor, and the other receiver is supplied with a pull-up voltage.

In order to solve the above problem, according to a sixth aspect of the present invention, there is provided the X-ray imaging apparatus according to the third aspect, wherein the plug is disposed in the accommodating section, and wherein the outlet is disposed in the detector panel.

In order to solve the above problem, according to a seventh aspect of the present invention, there is provided the X-ray imaging apparatus according to the fifth aspect, wherein the feeding control device discriminates the accommodation and non-accommodation according to the magnitude of a both-end voltage of the pull-down resistor.

In order to solve the above problem, according to an eighth aspect of the present invention, there is provided the X-ray imaging apparatus according to the first aspect, wherein the X-ray detector comprises a two-dimensional X-ray detector.

In order to solve the above problem, according to a ninth aspect of the present invention, there is provided the X-ray imaging apparatus according to the first aspect, wherein signal transmission and reception between the electronic circuit and the control circuit are performed in a wireless manner.

In order to solve the above problem, according to a tenth aspect of the present invention, there is provided the X-ray imaging apparatus according to the first aspect, wherein the battery comprises a secondary battery.

In order to solve the above problem, according to an eleventh aspect of the present invention, there is provided a portable detector panel used for X-ray photography, comprising: an X-ray detector; an interface electronic circuit; a power supply battery; and feeding control device for unexecuting and executing feeding to the electronic circuit from the battery according to the accommodation and non-accommodation of the detector panel to a given external place.

In order to solve the above problem, according to a twelfth aspect of the present invention, there is provided the portable detector panel according to the eleventh aspect, wherein the feeding control device includes a connection section that is electrically connected to the given external place.

In order to solve the above problem, according to a thirteenth aspect of the present invention, there is provided the portable detector panel according to the twelfth aspect, wherein the connection section comprises a plug or an outlet which corresponds to each other.

In order to solve the above problem, according to a fourteenth aspect of the present invention, there is provided the portable detector panel according to the twelfth or thirteenth aspect, wherein the connection section is disposed on an end surface of the detector panel.

In order to solve the above problem, according to a fifteenth aspect of the present invention, there is provided the portable detector panel according to the thirteenth aspect, wherein the plug has three parallel conductors, in which a center conductor is connected to the ground, and both-side conductors are commonly connected to each other, and wherein the outlet has three receivers corresponding to the conductors, in which a center receiver functions as a common receiver, one of the remaining two receivers is connected with a pull-down resistor, and the other receiver is applied with a pull-up voltage.

In order to solve the above problem, according to a sixteenth aspect of the present invention, there is provided the portable detector panel according to the thirteenth aspect, wherein an outlet is disposed as the connection section of the detector panel.

In order to solve the above problem, according to a seventeenth aspect of the present invention, there is provided the portable detector panel according to the fifteenth aspect, wherein the feeding control device discriminates the accommodation and non-accommodation according to the magnitude of a both-end voltage of the pull-down resistor.

In order to solve the above problem, according to an eighteenth aspect of the present invention, there is provided the portable detector panel according to the eleventh aspect, wherein the X-ray detector comprises a two-dimensional X-ray detector.

In order to solve the above problem, according to a nineteenth aspect of the present invention, there is provided the portable detector panel according to the eleventh aspect, wherein the electronic circuit can transmit and receive a signal by the control circuit in a wireless manner.

In order to solve the above problem, according to a twentieth aspect of the present invention, there is provided the portable detector panel according to the eleventh aspect, wherein the battery comprises a secondary battery.

According to the X-ray imaging apparatus and the portable detector panel, since the detector panel has the feeding control device for unexecuting and executing feeding to the electronic circuit from the battery according to the accommodation and non-accommodation in the accommodating section, respectively, it is possible to conduct the feeding and non-feeding to the load from a built-in battery in association with the use or nonuse of the detector panel.

DETAILED DESCRIPTION OF THE INVENTION

Figure 1:
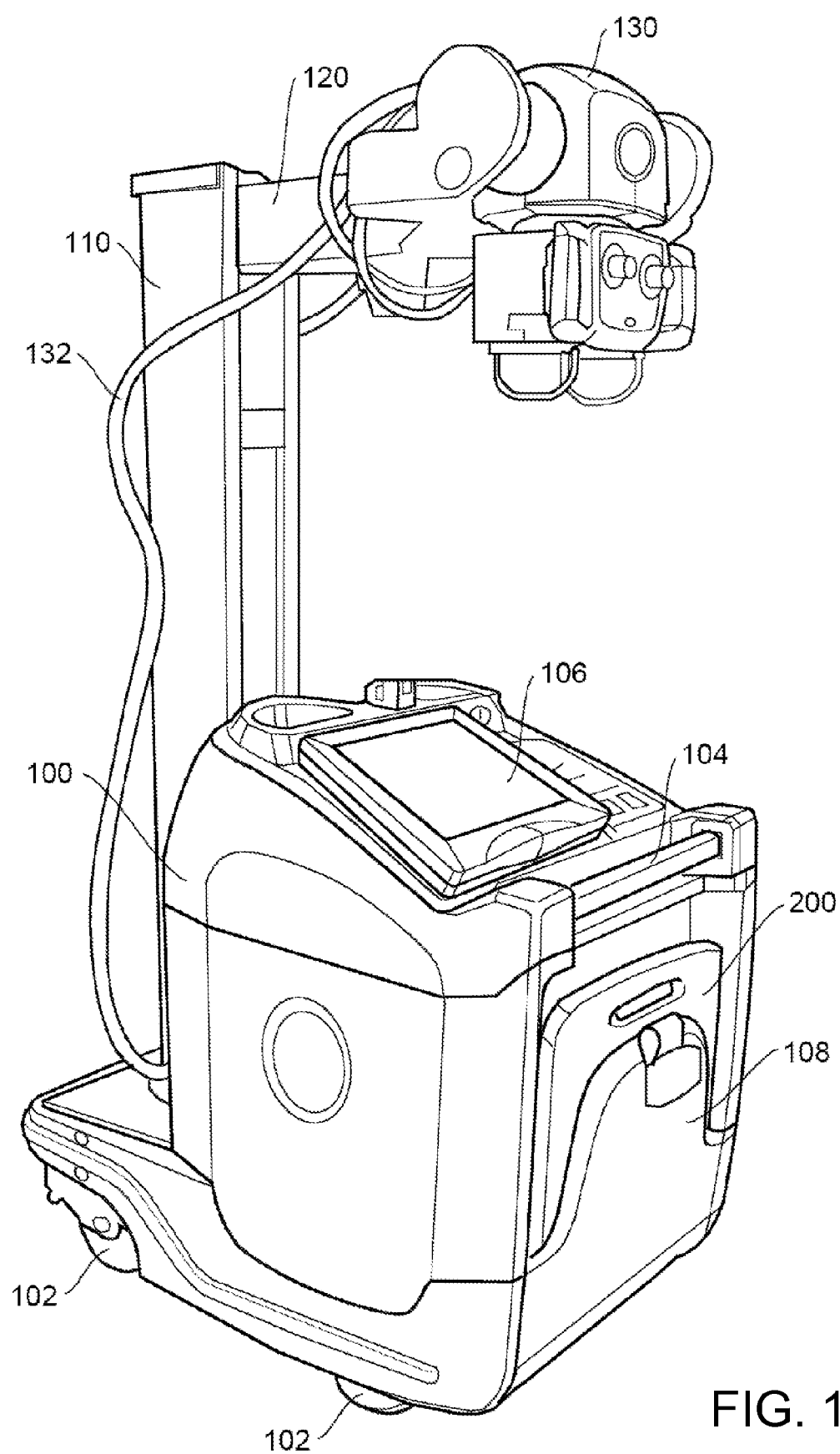
FIG. 1 is a diagram showing the appearance of an X-ray imaging apparatus according to an example of the best mode for carrying out the invention.

Hereinafter, a description will be given in detail of embodiments of the invention with reference to the drawings. The present invention is not limited to the embodiments described herein. FIG. 1 shows the appearance of the X-ray imaging apparatus. The configuration of this apparatus shows an example of the invention related to the X-ray imaging apparatus.

Figure 2:
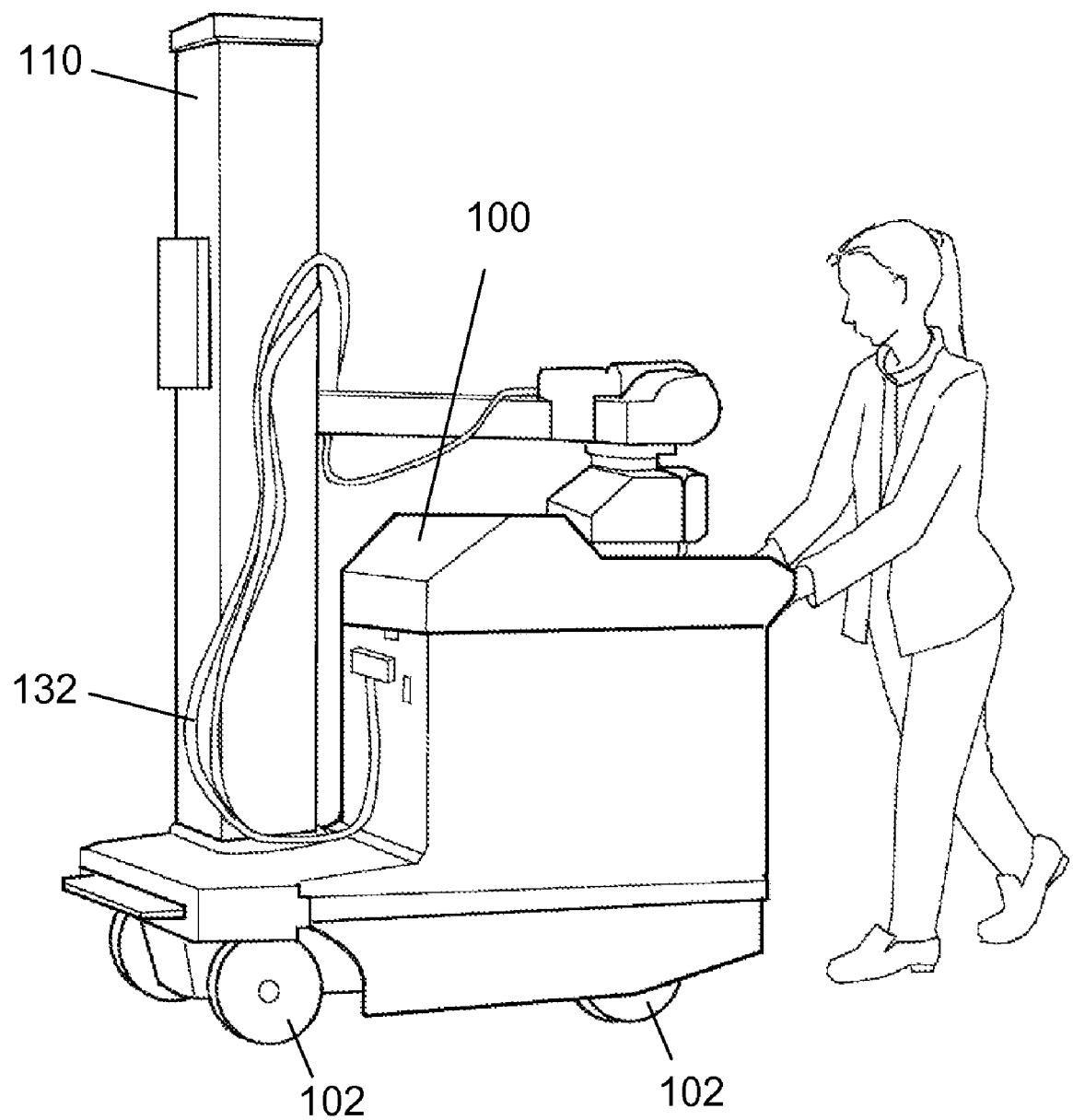
FIG. 2 is a diagram showing the appearance while the X-ray imaging apparatus according to the example of the best mode for carrying out the invention is moving.

As shown in FIG. 1, this apparatus includes a system console 100. The system console 100 is a box-type construction that is substantially rectangular parallelepiped, and has a photography control electronic circuit internally. The system console 100 has travel casters 102 at a lower portion thereof, and has a hand-grid handle 104 at a higher portion thereof. With the above configuration, this apparatus becomes a mobile X-ray imaging apparatus that can be freely moved as shown in FIG. 2.

The upper surface of the system console 100 is equipped with an operation panel 106 which includes a man-machine communication device such as a graphic display or a keyboard.

The back of the system console 100 is equipped with a column 110, and a leading end of an arm 120 that extends horizontally from the column 110 is equipped with an X-ray irradiator 130. The x-ray irradiator 130 generates X-rays due to a high voltage that is supplied from the system console 100 through a cable 132.

The X-ray irradiator 130 is capable of changing its direction at the leading end of the arm 120. The arm 120 is capable of moving vertically along the column 110, and the column 110 can be spin centered on the axis in the longitudinal direction.

This apparatus includes a detector panel 200. The detector panel 200 is of a construction of the substantially square plate, which is separate from the system console 100 so as to be portable. The detector panel 200 is accommodated in the accommodating section 108 which is in front of the system console 100 at time of non-photographing, and is extracted from the accommodating section 108 and used at the time of photographing.

Figure 3:
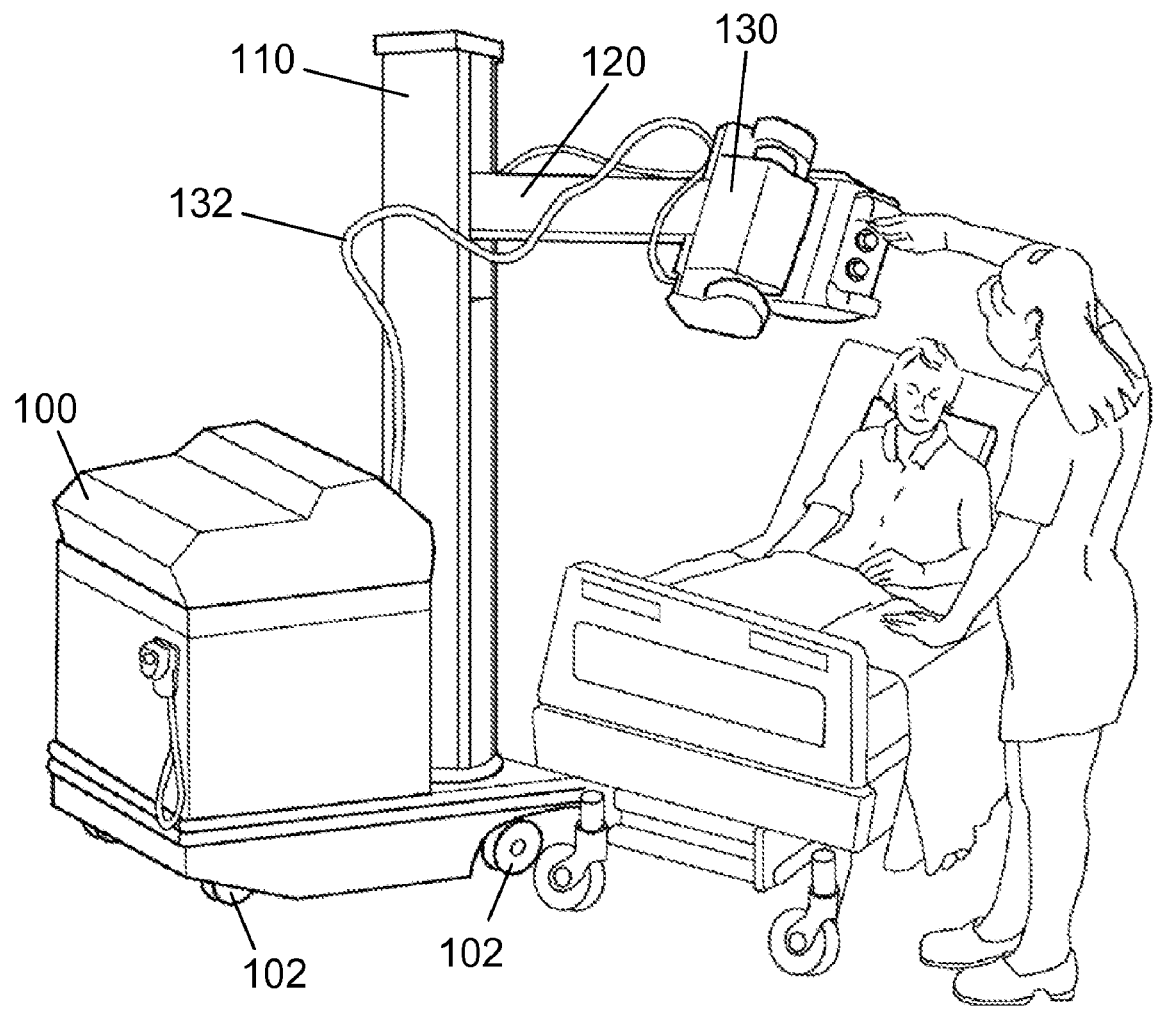
FIG. 3 is a diagram showing the appearance when a patient is photographed by the X-ray imaging apparatus according to the example of the best mode for carrying out the invention.

FIG. 3 shows a scene while this apparatus is being used. As shown in FIG. 3, the apparatus is used in the patient's room. The X-ray photography is conducted by applying the detector panel 200, for example, on a back of the patient, and irradiating a front of the patient with the X-rays by means of the X-ray irradiator 130 of the system console 100. The X-ray signal that has been detected by the detector panel 200 is transmitted to the system console 100 wirelessly.

Figure 4:
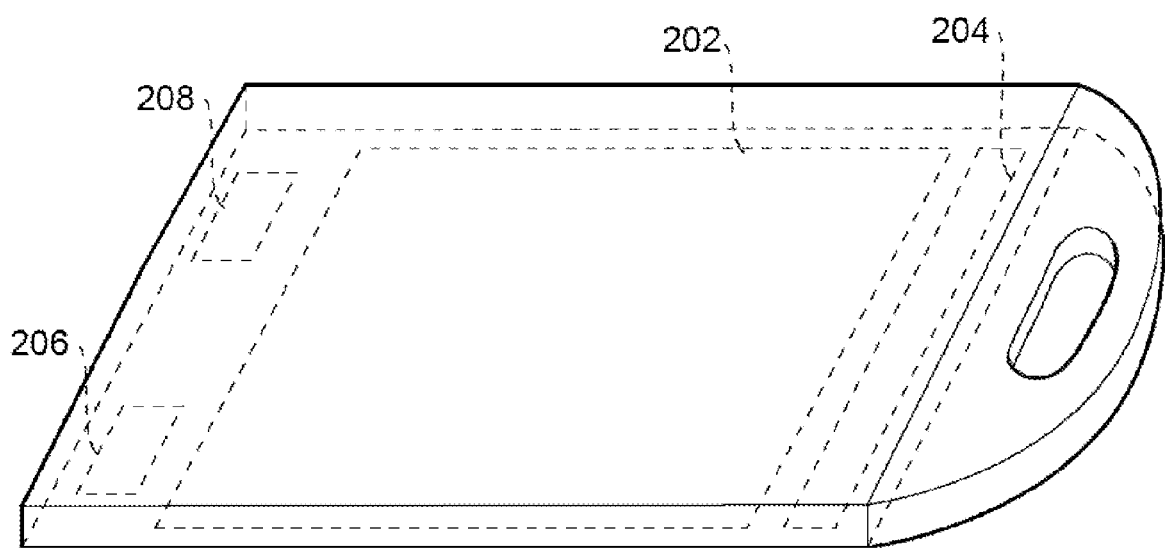
FIG. 4 is a diagram showing the configuration of a detector panel.

FIG. 4 schematically shows the configuration of the detector panel 200. As shown in FIG. 4, the detector panel 200 includes an X-ray detector 202, an interface circuit 204, a battery 206, and a feeding control circuit 208 therein.

The X-ray detector 202 is a two-dimensional X-ray detector which includes a large number of X-ray detection elements which are arranged in a matrix. The interface circuit 204 is a circuit that transmits and receive a signal with respect to the system console 100. The detection signal of the X-ray detector 202 is transmitted to the system console 100 through the interface circuit 204 wirelessly.

The battery 206 is a power supply of the detector panel 200. All of the electric circuits within the detector panel 200 are loads of the battery 206. The battery 206 to be used is, for example, a secondary battery. Since the secondary battery can be repetitively used by recharge, the secondary battery is convenient. The battery 206 may be a primary battery.

The feeding control circuit 208 controls the feeding to the load from the battery 206. The feeding control is conducted for the purpose of saving electricity. The electricity saving is conducted by feeding to all of the loads only when the detector panel 200 is used, and feeding to only the smallest number of loads as required when the detector panel 200 is not used. In the following description, the feeding to only the smallest number of loads as required is also called "hibernation".

The detector panel 200 is accommodated in the accommodating section 108 when the detector panel 200 is not used, and extracted from the accommodating section 108 when the detector panel 200 is used. In view of this fact, the hibernation and its cancel are conducted in association with the accommodation and non-accommodation of the detector panel 200 in the accommodating section 108 by means of the feeding control circuit 208. The feeding control circuit 208 is an example of the feeding control device according to the present invention.

Figure 5:
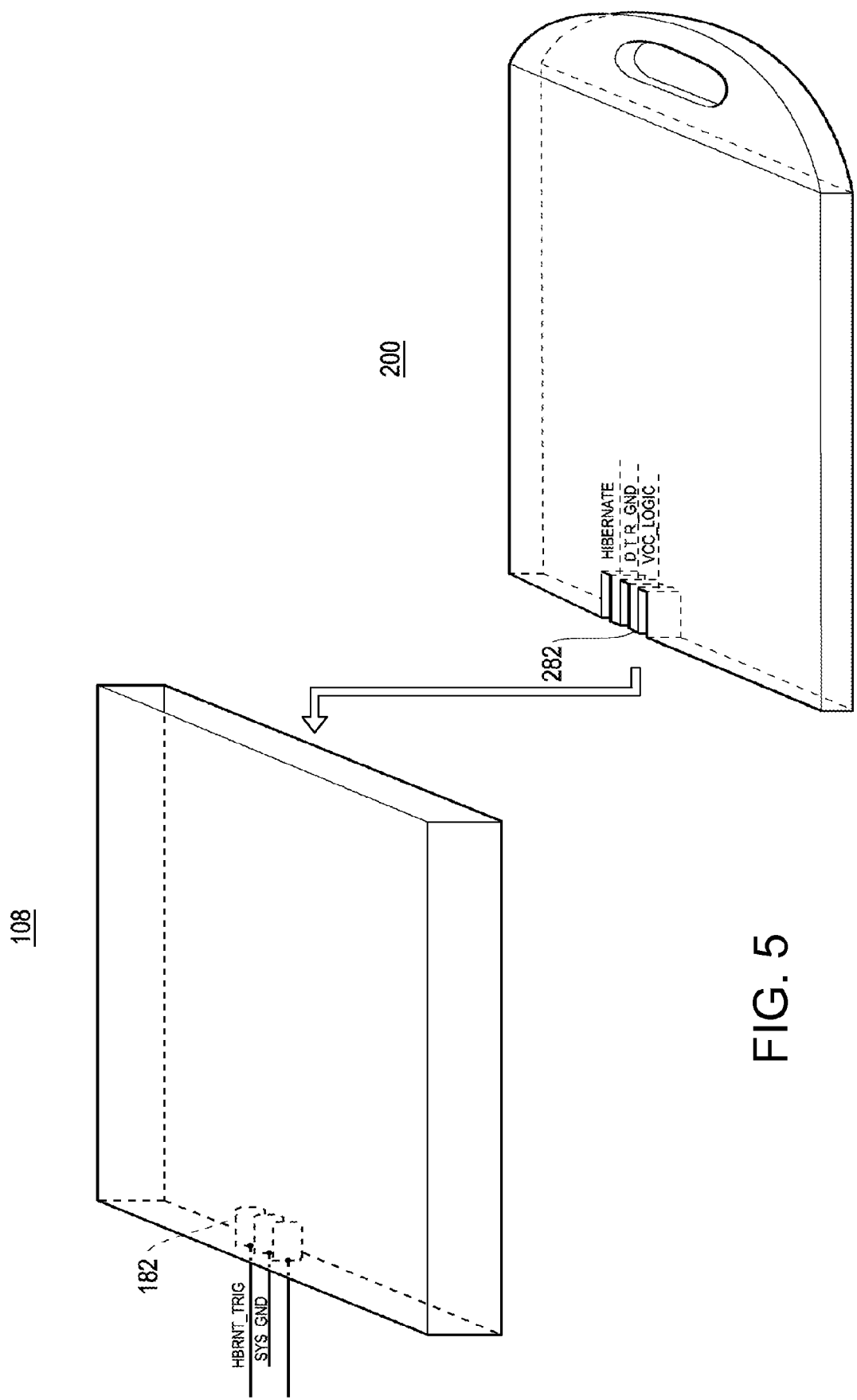
FIG. 5 is a diagram showing a relationship between the detector panel and an accommodating section.

Hereinafter, the feeding control in association with the accommodation and non-accommodation will be described. In order to enable the associated feeding control, as shown in FIG. 5, a plug 182 as an example of the connection portion of the accommodating section is disposed on the bottom of the accommodating section 108. The plug 182 is disposed in the center of the bottom of the accommodating section. The plug 182 can be disposed not in the center of the bottom, but disposed at any sided portion of the bottom.

Alternatively, the electric connection point of the surface contact system or other systems can be used instead of the plug 182. Those electric contacts can be disposed not only on the bottom of the accommodating section 108, but also appropriate portions that come in contact with the detector panel 200. In the following description, the plug is exemplified, but the same is applied to the electric contacts of other systems.

The plug 182 has three parallel conductors. Those three conductors are bilaterally symmetrical with respect to the center conductor. Those three conductors can be bilaterally asymmetrical. Three signal lines are extracted from the three conductors, respectively. The center signal line is a system ground line SYS_GND, and two other signal lines are hibernate trigger line HBRNT_TRIG that are commonly connected to each other.

The end surface of the detector panel 200 is equipped with an outlet 282 as an example of the connection section as an example of the connection section of the detector panel. The end surface is a portion that is abutted against the bottom of the accommodating section 108 when the detector panel 200 is accommodated. The outlet 282 is paired with the plug 182. When the plug 182 is disposed in the center of the bottom of the accommodating section 108, the outlet 282 is also disposed in the center of the end surface. When the plug 182 is disposed not in the center of the bottom of the accommodating section 108, but on any one side of the bottom, the outlet 282 is also disposed on a corresponding side.

Alternatively, when the electric connection point of the surface contact system or other systems can be used instead of the plug 182, the electric connection point of the surface contact system or other systems can be used instead of the outlet 282. Those electric contacts can be disposed not only on the end surface of the detector panel 200, but also on appropriate portions that come in contact with the accommodating section 108. In the following description, the outlet is exemplified, but the same is applied to the electric contacts of other systems. Also, the plug 183 can be disposed in the detector panel, and the outlet 282 can be disposed in the accommodating section 108.

The outlet 282 has three parallel receivers. The three receivers are bilaterally symmetrical with respect to the center receiver. When the three conductors of the plug 182 can be bilaterally asymmetrical, the three conductors are also asymmetrical in correspondence with those conductors.

Three signal lines are extracted from the three receivers, respectively. The center signal line is a detector ground line DTR_GND, and two other signal lines are a hibernate line HIBERNATE and VCC logic line VCC_LOGIC.

With the above configuration of the plug 182 and the outlet 282, the detector ground line DTR_GND is connected to a system ground line SYS_GND when the detector panel 200 is accommodated, and both of the hibernate line HIBERNATE and the VCC logic line VCC_LOGIC are connected to the hibernate trigger line HBRNT_TRIG.

Figure 6:
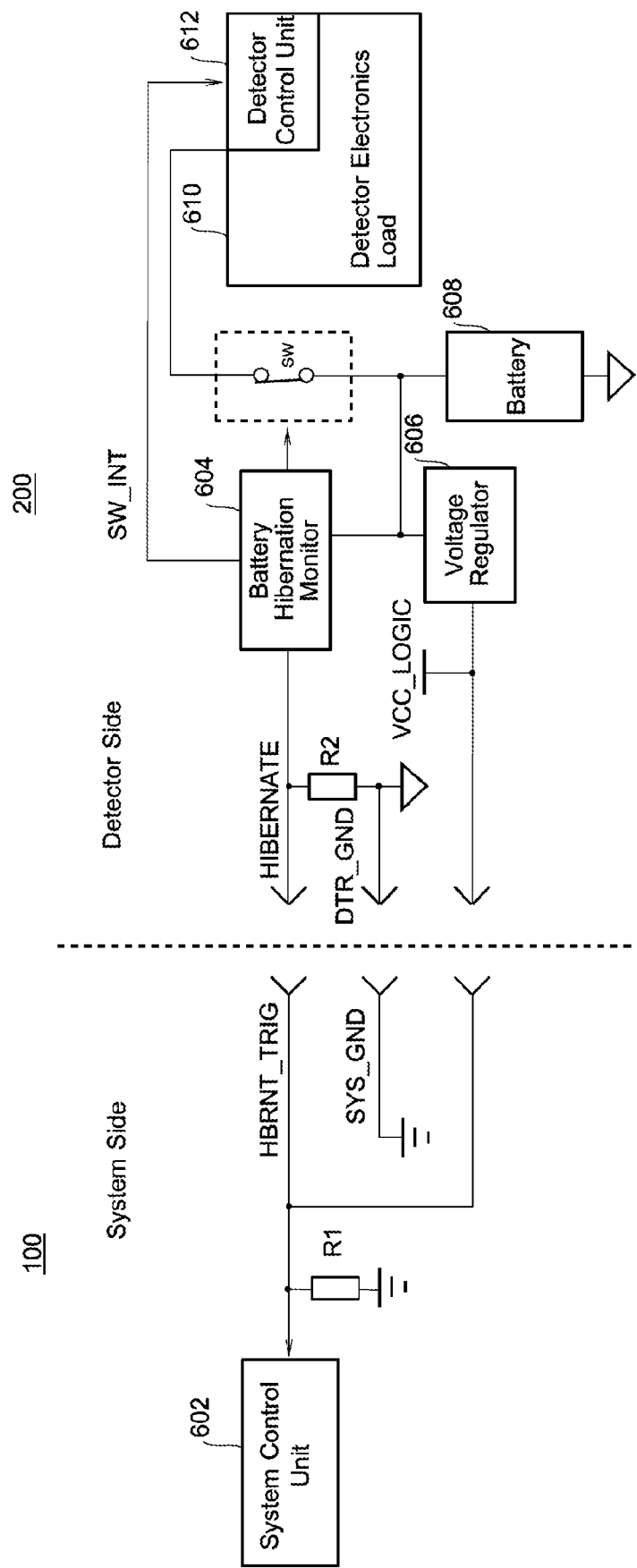
FIG. 6 is a diagram showing an electric structure of a portion related to a feeding control.

FIG. 6 shows an example of the configuration of the feeding control circuit 208. As shown in FIG. 6, at the system console 100 side, the system ground line SYS_GND is connected to the system ground, and the hibernate trigger line HBRNT_TRIG is connected to the system ground through a pull down resistor R1. A both-end voltage of the pull down resistor R1 is input to the system control unit 602.

At the detector panel 200 side, the detector ground line DTR_GND is connected to the detector ground, and the hibernate line HIBERNATE is connected to the detector ground through a pull down resistor R2. A both-end voltage of the pull down resistor R2 is input to a battery hibernation monitor 604. The VCC logic line VCC_LOGIC is supplied with a VCC logic voltage that is output from a voltage regulator 606.

The battery hibernation monitor 604 and the voltage regulator 606 are supplied with a supply voltage from a battery 608. The supply voltage from the battery 608 is also supplied to a detector electronics load 610 through a switch SW. The switch SW can be a solid state switch such as an FET.

The detector electronics load 610 includes the X-ray detector 202 and the interface circuit 204. The detector electronics load 610 also includes a detector control unit 612. The detector control unit 612 retreats or restores internal data according to on/off of the switch SW. A nonvolatile memory is used for retreating and restoring the internal data.

The on/off operation of the switch SW is controlled by the battery hibernation monitor 604. When the switch SW is on/off, an interrupt signal SW_INT is issued to the detector control unit 612 from the battery hibernation monitor 604.

The circuit state shown in FIG. 6 is a state in which the detector panel 200 is not accommodated. The plug 182 and the outlet 282 are not coupled with each other, as a result of which at the system console 100 side, the both-end voltage of the pull-down resistor R1 is 0. On the basis of this voltage, the system control unit 602 recognizes the non-accommodation of the detector panel 200. When it is unnecessary that the system control unit 602 recognizes the accommodation and the non-accommodation of the detector panel 200, no signal input circuit using the pull down resistor R1 is required.

At the detector panel 200 side, the both-end voltage of the pull down resistor R2 is 0, and the switch SW turns on by the battery hibernation monitor 604 having the both-end voltage as an input signal. As a result, the power is supplied to the detector electronics load 610 from the battery 206.

Figure 7:
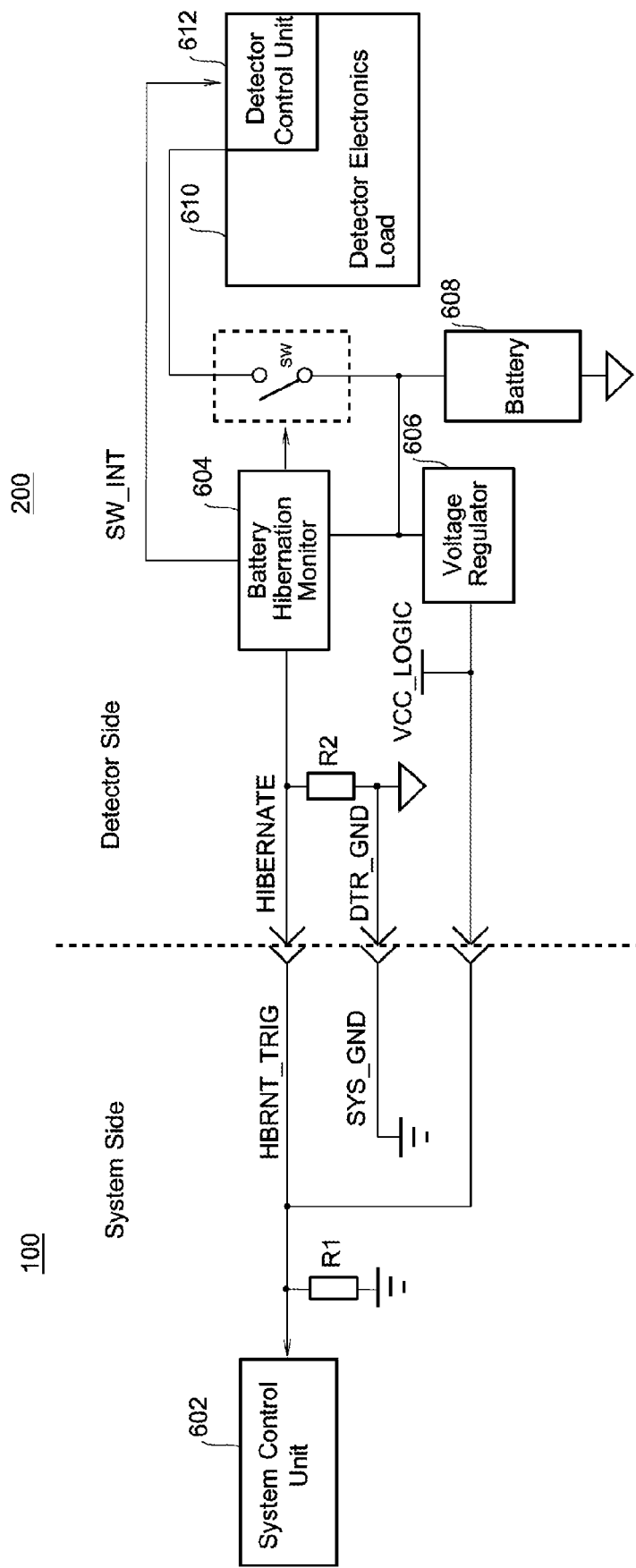
FIG. 7 is a diagram showing an electric structure of a portion related to a feeding control.

FIG. 7 shows a circuit state when the detector panel 200 is accommodated. The plug 182 and the outlet 282 are coupled with each other, whereby the VCC logic voltage is applied to the hibernate line HIBERNATE through the hibernate trigger line HBRNT_TRIG.

For that reason, at the system console 100 side, the both-end voltage of the pull down resistor R1 is a VCC logic voltage, and on the basis of the voltage, the system control unit 602 recognizes the accommodation of the detector panel 200. When it is unnecessary that the system control unit 602 recognizes the accommodation and the non-accommodation of the detector panel 200, no signal input circuit using the pull down resistor R1 is required.

At the detector panel 200 side, the both-end voltage of the pull down resistor R2 is the VCC logic voltage, and the switch SW turns off by the battery hibernation monitor 604 having the both-end voltage as an input signal. As a result, the feeding to the detector electronics load 610 from the battery 206 is blocked.

In this state, the feeding from the battery 608 is conducted on only the battery hibernation monitor 604 and the voltage regulator 606. That is, the feeding is conducted on only the smallest number of loads to come to a hibernation state.

The internal data is retreated by the detector control unit 612 on the basis of the interrupt signal SW_INT which is issued from the battery hibernation monitor 604 prior to the feeding block.

When the detector panel 200 is extracted from the accommodating section 108, the circuit returns to a state shown in FIG. 6. In this situation, at the detector panel 200 side, the both-end voltage of the pull down resistor R2 is 0, and the switch SW turns on by the battery hibernation monitor 604, and the feeding to the detector electronics load 610 from the battery 206 is restarted.

With the restart of feeding, the internal data is restored by the detector control unit 612 on the basis of the interrupt signal SW_INT that is issued from the battery hibernation monitor 604. In the following description, likewise, the hibernation of the battery 206 and its cancel are conducted in association with the accommodation and the non-accommodation of the detector panel 200 in the accommodating section 108.

What is claimed is:

1. An X-ray imaging apparatus comprising:
a mobile system console comprising:
an X-ray irradiator;
a control circuit; and
an accommodating section: and
a portable detector panel sized to be housed in said accommodating section at a time of nonuse, said detector panel comprising:
an X-ray detector;
an interface electronic circuit;
a power supply battery; and
a feeding control device configured to control power supply to said electronic circuit from said battery based on whether said detector panel is housed in said accommodating section.

2. The X-ray imaging apparatus according to claim 1, wherein said accommodating section and said detector panel respectively comprise connection sections that are electrically connected to each other when said detector panel is housed in said accommodating section.

3. The X-ray imaging apparatus according to claim 2, wherein said accommodating section further comprises one of a plug and an outlet, and said detector panel further comprises one of an outlet and a plug corresponding to said one of said plug and said outlet of said accommodating section.

4. The X-ray imaging apparatus according to claim 2, wherein said connection section of said accommodating section is disposed on a bottom surface of said accommodating section, and said connection section of said detector panel is disposed on an end surface of said detector panel which is configured to abut against the bottom surface of said accommodating section.

5. The X-ray imaging apparatus according to claim 3, wherein said plug comprises a center conductor connected to ground, and a plurality of side conductors commonly connected to each other, and wherein said outlet comprises a center receiver configured as a common receiver, a first side receiver connected with a pull-down resistor, and a second side receiver supplied with a pull-up voltage.

6. The X-ray imaging apparatus according to claim 3, wherein said plug is disposed in said accommodating section, said outlet is disposed in said detector panel.

7. The X-ray imaging apparatus according to claim 5, wherein said feeding control device is configured to determine whether said detector panel is housed in said accommodating section based on a magnitude of a voltage of said pull-down resistor.

8. The X-ray imaging apparatus according to claim 1, wherein said X-ray detector comprises a two-dimensional X-ray detector.

9. The X-ray imaging apparatus according to claim 1, wherein signal transmission and reception between said electronic circuit and said control circuit are performed in a wireless manner.

10. The X-ray imaging apparatus according to claim 1, wherein said battery comprises a secondary battery.

11. A portable detector panel used for X-ray photography, comprising:
an X-ray detector;
an interface electronic circuit;
a power supply battery; and
a feeding control device configured to control power supplied to said electronic circuit from said battery based on whether said detector panel is housed within a given external place.

12. The portable detector panel according to claim 11, wherein said feeding control device comprises a connection section that is electrically connected to the given external place.

13. The portable detector panel according to claim 12, wherein said connection section comprises one of a plug and an outlet which corresponds to each other.

14. The portable detector panel according to claim 12, wherein said connection section is disposed on an end surface of said detector panel.

15. The portable detector panel according to claim 13, wherein said plug comprises a center conductor connected to ground, and a plurality of side conductors commonly connected to each other, and wherein said outlet comprises a center receiver configured as a common receiver, a first side receiver connected with a pull-down resistor, and a second side receiver supplied with a pull-up voltage.

16. The portable detector panel according to claim 13, wherein an outlet is disposed as said connection section of said detector panel.

17. The portable detector panel according to claim 15, wherein said feeding control device is configured to determine whether said detector panel is housed in the given external place based on a magnitude of a voltage of said pull-down resistor.

18. The portable detector panel according to claim 11, wherein said X-ray detector comprises a two-dimensional X-ray detector.

19. The portable detector panel according to claim 11, wherein said electronic circuit is configured to transmit and receive a signal by said control circuit in a wireless manner.

20. The portable detector panel according to claim 11, wherein said battery comprises a secondary battery.

* * * * *